United States Patent [19]

Kaufhold

[11] Patent Number: 4,642,405
[45] Date of Patent: Feb. 10, 1987

[54] PROCESS FOR THE PRODUCTION OF METHALLYLBENZENE AND ISOBUTENYLBENZENE AND THEIR P-SUBSTITUTED ALKYL DERIVATIVES

[75] Inventor: Manfred Kaufhold, Marl, Fed. Rep. of Germany

[73] Assignee: Huels Aktiengesellschaft, Marl, Fed. Rep. of Germany

[21] Appl. No.: 830,170

[22] Filed: Feb. 18, 1986

[30] Foreign Application Priority Data

Feb. 15, 1985 [DE] Fed. Rep. of Germany ....... 3505156

[51] Int. Cl.⁴ .......................... C07C 5/09; C07C 1/253
[52] U.S. Cl. ...................................... 585/435; 585/436
[58] Field of Search ................................ 585/435, 436

[56] References Cited

U.S. PATENT DOCUMENTS 2,454,779 11/1948 Davidson et al. .................... 585/436
4,556,754 12/1985 Kampf et al. ........................ 585/664

Primary Examiner—Curtis R. Davis
Attorney, Agent, or Firm—Millen & White

[57] ABSTRACT

For the preparation of methallylbenzene ($\alpha$-olefin) and isobutenylbenzene ($\beta$-olefin), and their p-substituted alkyl derivatives of Formulae 1 and 2, respectively, thermal cracking of neophyl chloride and the corresponding p-substituted neophyl chlorides of Formula 3 is performed, in the presence of an inhibitor for radical polymerization, with the resultant cracked product olefins of Formula 2 then isomerized to the corresponding $\alpha$-olefin of Formula 1 by a further distillation in the presence of a mixture containing a basic compound and a polar solvent.

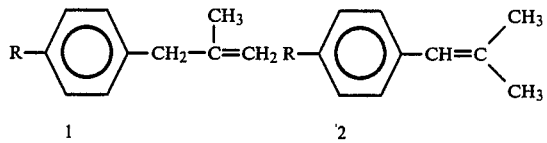

$R = H, -CH_3, CH_3CH_2-,$

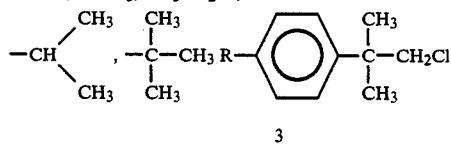

25 Claims, No Drawings

PROCESS FOR THE PRODUCTION OF METHALLYLBENZENE AND ISOBUTENYLBENZENE AND THEIR P-SUBSTITUTED ALKYL DERIVATIVES

BACKGROUND OF THE INVENTION

The invention relates to a process for the production of substantially pure methallylbenzene, isobutenylbenzene, and their p-substituted alkyl derivatives of Formula 1 and 2, respectively, by a process for the thermal cracking of neophyl chloride and the corresponding p-substituted neophyl chlorides of Formula 3, and if desired a subsequent isomerization of the cracked $\beta$-olefins of Formula 2 to the corresponding $\alpha$-olefin of Formula 2, while undergoing fractional distillation.

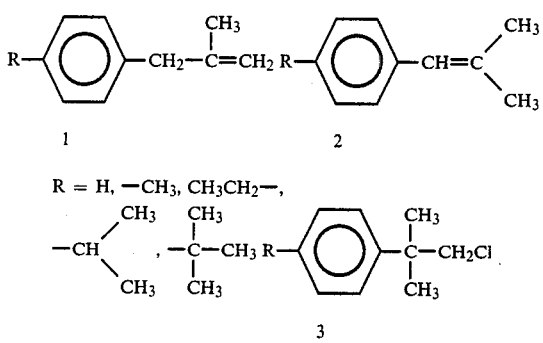

DESCRIPTION OF THE PRIOR ART

Syntheses of methallylbenzene, isobutenylbenzene and their p-substituted alkyl derivatives, using the readily obtainable neophyl chloride and/or its derivatives as starting materials, are disclosed in the literature.

Thus, Whitmore, Weisgerber and Shabica (*Am. Soc.* 65 [1943]: 1469, 1470) describe thermal cracking of neophyl chloride to methallylbenzene and isobutenylbenzene; they obtained a pyrolysis product having the following composition:

| | |
|---|---|
| methallylbenzene | 23.5% |
| isobutenylbenzene | 36.5% |
| neophyl chloride | 26.0% |
| 1-phenyl-2,2-dimethylethyl chloride | 8.9% |

An improved yield of 83% of olefin product mixture is obtained by means of a process disclosed in East German Pat. No. 99,358, wherein unreacted neophyl chloride is constantly recycled into the cracking installation. As demonstrated in the patent's example, the pyrolysis product contains, in addition to unreacted neophyl chloride, a relatively large amount (more than 10% of the olefin mixture) of undesirable residue.

The production and cracking of p-substituted alkyl derivatives of neophyl chloride are described in U.S. Pat. No. 2,454,779. As contrasted with the two above-cited references, this process pursues the express goal of controlling the thermal cracking whereby methallylbenzene and/or its derivatives, i.e., the $\alpha$-olefins, are formed as the primary product, instead of isobutenylbenzene and/or its derivatives, i.e., the $\beta$-olefins, as in the abovementioned literature references. This is because the $\alpha$-olefins are desirable as starting compounds in the manufacture of fragrances, which are of considerably greater importance than their isomers, the $\beta$-olefins.

The desired effect on the isomer proportion is obtained in the above-cited U.S. patent by conducting pyrolysis in the presence of stoichiometric amounts of an alkali metal salt of a carboxylic acid. The thus-obtained isomer proportions range, according to the disclosure in the examples, from about 3:1 to 4:1 for $\alpha:\beta$ olefin. Therefore, even in the most favorable case, the undesired $\beta$-olefin is formed in relatively large amounts and consequently renders the process uneconomical. Additionally, utilizing the alkali metal salts of carboxylic acids has the drawbacks that precious reactor space is occupied and also that sodium chloride is produced which must be discarded as waste.

Processes for the particular isomerization of isobutenylbenzene to methallylbenzene have not been known heretofore. In general, however, a variety of catalysts is employed for other isomerizations involving a shifting of the double bonds. Thus, for example, in a process for the positional isomerization of terminal-positioned double bonds in olefins (European Pat. No. 0 042 537), strongly acidic cation exchangers are utilized as the catalysts. In contrast thereto, the process of DOS No. 3,319,171 discloses the isomerization of butene-2 to butene-1, utilizing a similar equilibrium reaction as in European Pat. No. 0 042 537, but employs metallic oxides selected from either Group IIA, VIII and/or IIIB on $\gamma$-alumina.

Accordingly, all the prior art processes yield olefin mixtures, thus requiring both a large amount of starting material and also presenting problems with waste elimination. A process would be desirable in which the p-alkyl neophyl chloride, industrially easily obtainable by reacting methallyl chloride with the corresponding alkyl aromatic, is converted, without formation of significant amounts of waste products, into an olefin mixture, from which the valuable $\alpha$-olefin could be isolated, e.g., by distillation, and the undesired $\beta$-olefin can also be converted into the $\alpha$-olefin.

OBJECTS OF THE INVENTION

Accordingly, it is an object of this invention to provide, with low consumption of starting materials, for the production of substantially pure isobutenylbenzene and especially methallylbenzene and its p-alkyl containing derivatives from neophyl chloride and the corresponding p-alkyl neophyl chloride derivatives, because these $\alpha$-olefins are desirable raw materials which are utilized for the manufacture of fragrances, such as, p-tert-butyl-$\alpha$-methyldihydrocinnamaldehyde (also sold under the name "Lilial", a registered trademark of Givaudan.)

Upon further study of the specification and appended claims, further objects and advantages of this invention will become apparent to those skilled in the art.

SUMMARY OF THE INVENTION

Surprisingly, these and other objects have been attained through the discovery in a process for the production of substantially pure methallylbenzene ($\alpha$-isomer), isobutenylbenzene ($\beta$-isomer) and their p-substituted alkyl derivatives (Formulae 1 and 2, respectively) by the thermal cracking of neophyl chloride or the corresponding p-substituted neophyl chloride derivative (Formula 3), of the improvement comprising thermally cracking said neophyl chloride or p-substituted derivative at about 150°–350° C. in the presence of an effective inhibitor of free radical polymerization; isomerizing the formed isobutenylbenzene and its p-substituted alkyl derivatives (Formula 2) by heating, preferably at about 80°–300° C. and thereby forming the corresponding α-olefin (Formula 1).

Surprisingly, substantially better yields are obtained in the thermal cracking of neophyl chloride and p-alkyl neophyl chlorides than in the above-identified East German Pat. No. 99,358, by conducting the cracking step in the presence of an effective inhibitor of free radical polymerization.

Furthermore, methallylbenzene and its p-alkyl containing derivatives are obtained in a surprisingly simple manner from the resulting cracked olefin mixture by effecting isomerization by addition of suitable basic compounds and suitable polar solvents followed by separating the desired, lower-boiling α-olefin by suitable means, e.g., fractional distillation.

It has also been found, surprisingly, that by conducting the isomerization process as required herein, a further purification of the cracked olefins is also achieved, wherein the residual chlorine content, e.g., usually 200–300 ppm is lowered to below about 10 ppm. Such a reduction in chlorine content is, because of the danger of corrosion, a necessary prerequisite for the further processing of the α-olefin products obtained in commercial apparatus built from industrial materials such as, for example, stainless steel V4A, (austenitic steel; 18% Cr, 8% Ni, 2% Mo).

DETAILED DESCRIPTION

The improved yields and conversions obtained by thermally cracking neophyl chloride and its p-alkyl derivatives in the presence of a suitable inhibitor for free radical polymerization (i.e., of alkenes to form oligo- or polyolefins) was surprising since if anything it was only to be expected that the amount of high-boiling compounds produced would be decreased due to suppressed polymerization of double bonds; it could not have been expected that the thermal cracking step per se would be enhanced. According to the process of this invention, conversion rates of neophyl chloride of above 95% and yields of α and β-olefin, based on conversion, of at least 98% are attained, whereas in Example 1 of the aforementioned East German Pat. No. 99,358 a yield of merely 66.5% of olefin mixture, based on neophyl chloride, is disclosed. In cracking p-tert-butylneophyl chloride, the conversion rates in the process of this invention are even higher, i.e., about 99.9%, which is almost quantitative.

Suitable inhibitors are those compounds customarily employed for prevention of free radical polymerization, such as, for example, phenoles, aminophenoles, aminothiophenoles and phenylendiamines and their derivates such as tert-butylpyrocatechol, hydroquinone, or 2,6-di-tert-butylphenol, p-oxidiphenol, p-oxiphenylcyclohexylamin, phenothiazine, etc. various mixtures and the like. For additional inhibitors, see Ullmanns Encyklopaedie der technischen Chemie [Ullmann's Encyclopedia of Industrial Chemistry] 14:116, 3rd Ed., publishers Urban and Schwarzenberg, Munich-Berlin, 1963), the disclosure of which is incorporated by reference.

The inhibitor concentration is about 0.01–5%, preferably about 0.1–1%. Thermal cracking takes place at about 150°–350° C., preferably about 180°–300° C. for about 6–10 hours in general. Cracking is performed generally at atmospheric pressure, but can also be conducted in the excess pressure and vacuum regions, if desired. The cracking reaction can be undertaken both continuously and in a batch mode.

A significant advantage of the process of the invention is that the isomerization of the olefin mixture to the α-olefin can occur in conjunction with the simultaneous distillatory separation of the newly formed α-olefin from the reaction mixture. This synthesis step effectively solves the problem of high losses in feed materials discussed, supra, since the β-olefin reaction product can be effectively recycled and isomerized to the desired α-olefin.

The catalysts heretofore proposed for the isomerization of α- and β-olefins have proved unsuitable in the isomerzation of isobutenylbenzene to methallylbenzene, i.e., the isomerization of a β-olefin to an α-olefin. Surprisingly, excellent results have been achieved by incorporating members of a class of strongly basic compounds into the catalyst system. Suitable basic catalysts comprise alkali metal hydroxides, such as LiOH, NaOH, KOH, RbOH and CsOH, and mixtures thereof and other soluble metal hydroxides, such as $Ca(OH)_2$, $Sr(OH)_2$, $Ba(OH)_2$, and mixtures there of, Lanthanides, such as $Ce(OH)_3$, amines, aminoalcohols with higher boiling point than the olefines, and other suluble basic compounds.

The most preferred basic compounds are sodium and/or potassium hydroxide. The catalyst system further includes the presence of a polar solvent such as, for example, at least one member of the class of alcohols, diols, polyols, glycol ethers and/or polar aprotic compounds with dipols over 1,5 Debye and parameters of polarity greater than 0,01.

Preferably, the polar solvents employed are alcohols, e.g., aliphatic ones such as methanol, ethanol, propanol, isopropanol and most preferably, higher-boiling alcohols, such as isobutanol, tert-butanol, n-butanol, n- and isoamyl alcohols, and the like. Preferred polar aprotic compounds are dimethyl sulfoxide, dimethylformamide, N-methylpyrrolidone, alkyl glycol ethers with $C_1$- to $C_4$-alkyl groups, e.g., butyl diglycol and butyl triglycol, which are particularly effective in conjunction with sodium hydroxide as the alkaline compound; polyglycols and/or polyethylene glycol diethers of the general formula $R-O-(-CH_2-CH_2O)_n-R$ wherein $n=1$ to 20 and $R=C_{1-4}$-alkyl, etc. The most preferred polar solvent composition is butyl diglycol.

The basic compound is utilized in amounts ranging from about 0.1–50%, based on the olefin mixture to be isomerized, preferably 0.5–5%.

The polar solvent is generally employed in amounts of about 1–50%, based on the olefin mixture to be isomerized, preferably 1–10%.

These strongly basic catalyst systems have been used heretofore only in an isomerization of a chemically different system, i.e., the isomerization of isolated double bonds to form conjugated double bonds in low-molecular weight homo- and/or copolymers of 1,3-dienes (DOS's Nos. 3,205,990, 3,227,684 and 3,227,685).

Isomerization is generally conducted by heating, preferably at temperatures of about 80°–300° C., most preferably at 180°–300° C. for about 5–10 hours in general, depending on reaction conditions. If desired, the inhibitors employed in the cracking step can be utilized in the isomerization operation. The inhibitors stop the polymerization. After the reactions the inhibitors are rejected.

The process of this invention can be performed in a particular preferred embodiment: The starting materials chosen are neophyl chloride and/or a p-alkyl neophyl chloride. These reactants can be formed, if desired, from the reaction of methallyl chloride with benzene, or the corresponding alkyl benzene, in the presence of sulfuric acid as the catalyst (as for the synthesis of neophyl chloride, see, for example, *Organic Syntheses,* Collective Volume 4 [Annual V. 30–39], John Wiley and Sons, Inc., 1963, p. 702; as for p-alkyl neophyl chloride syntheses, see the above-cited U.S. Pat. No. 2,454,779); the particular neophyl chloride product formed being subsequently purified by distillation or recrystallization. The thermal cracking is performed under normal pressure or slightly superatmospheric pressures, for example, from 1–20 bar, preferably 1–5 bar. The process can, if desired, be conducted as a distillation wherein the low-boiling cracked olefin products are discharged "overhead" along with the thus-formed gaseous hydrogen chloride, while the unreacted neophyl chloride (or p-alkyl neophyl chloride) is recycled, e.g., through the adjusted backflow to the hot sump. The reactant compound can be heated either in the absence or presence of a solvent, in which case the cracked products, but not the by-product hydrogen chloride, are retained by means of a cooler. The sump temperatures of the distillation apparatus range between about 150° and 350° C., preferably 180°–300° C. Prior to cracking, an inhibitor is added to the chloride containing reactant, serving ordinarily for the prevention of radical polymerizations, for example, tertbutylpyrocatechol. The concentration of inhibitor is about 0.01–5%, preferably 0.1–1%.

If desired, the cracked olefins are purified by distillation and separated from the unreacted starting material, although in another embodiment the cracked olefins can be directly and continuously passed to the isomerization stage.

The isomer interchange of the cracked olefins takes place in a second distillation apparatus further containing suitable polar solvent, e.g., isobutanol, and a strong base, e.g., potassium hydroxide, in the sump of the apparatus. The concentrations of these additions are 1–10%, while the temperatures utilized range from about 80° to 300° C., preferably 180°–300° C. An inhibitor utilized in the isomerization step may also be present, up to 5%, if desired, preferably 0,1–1%.

As in any distillation, the particular pressure employed is dependent on the particular temperatures utilized. For example, the mixture of methallylbenzene and isobutenylbenzene can be isomerized under atmospheric pressure, resulting in sump temperatures of 185°–295° C. and head temperatures of 92°–182° C. In contrast, the temperatures utilized in the isomerization of p-tert-butylisobutenylbenzene, under atmospheric pressure, are 232°–300° C. in the sump and 88°–241° C. at the head while, under a vacuum of 250 mbar, sump temperatures of 196°–224° C. and head temperatures of 64°–195° C. are measured.

The desired α-olefins, methallylbenzene or p-alkyl methallylbenzene, produced are particularly suitable for the manufacture of fragrances, such as, for example, p-tert-butyl-α-methyldihydrocinnamic aldehyde, and also can be valuable intermediates in numerous other industrial syntheses.

R in the general formula can also be an other group, such as halogen, hydroxyl, amino and so on.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1a—THERMAL CRACKING

A glass apparatus is utilized consisting of a three-necked flask with stirrer, thermometer, and a distillation column with distillation head.

The following materials are employed:
300 g of neophyl chloride (99.0% strength)
1 g of tert-butylpyrocatechol A nitrogen stream is passed at a rate of 2 l/h through this mixture. The temperature is then raised to 190° C. and cracking is initiated, as can be seen from the evolution of gas. As indicated in the table below, no product is initially removed by distillation; rather, the mixture is heated under reflux to 210° C.

The further course of the temperature can be seen from the table.

| Reaction Time in h | Temperatures (°C.) Sump | Jacket | Head | Ratio Reflux:Discharge | N₂ Stream l/h |
|---|---|---|---|---|---|
| Beginning | 190 | 160 | — | No Discharge | 2 |
| 0.5 | 212 | 160 | 172 | No Discharge | 2 |
| 1 | 210 | 160 | 175 | No Discharge | 2 |
| 1.5 | 208 | 160 | 178 | 5:1 | 2 |
| 2 | 212 | 160 | 181 | 5:1 | 2 |
| 2.5 | 213 | 160 | 182 | 5:1 | 2 |
| 3 | 214 | 160 | 182 | 5:1 | 2 |
| 3.5 | 215 | 160 | 178 | 5:1 | 2 |
| 4 | 216 | 160 | 173 | 5:1 | 2 |
| 4.5 | 212 | 160 | 182 | 5:1 | 2 |
| 5 | 212 | 160 | 181 | 5:1 | 2 |
| 5.5 | 228 | 160 | 180 | 20:1 | 2 |
| 6 | 248 | 160 | 178 | 20:1 | 2 |
| 6.5 | 296 | 160 | 180 | 20:1 | 2 |
| 7 | 300 | 160 | 180 | 20:1 | 2 |
| 7.5 | 296 | 175 | 178 | 20:1 | 2 |
| 8 | 296 | 175 | 172 | Complete Discharge | 6 |
| 8.25 | 296 | 175 | 160 | Complete Discharge | 6 |

232 g of distillate is obtained, representing cracked products; 7 g is present in the column and 6 g remains in the sump as high-boiling compounds.

The distillate, washed neutral, has a chlorine content of 1.9% and has the following composition in accordance with GC analysis:

| | |
|---|---|
| 1-Phenyl-2-methyl-2-propene (1): | 33.4% |
| 1-Phenyl-2-methyl-1-propene (2): | 60.4% |
| 1-Phenyl-2-methyl-2-chloropropane: | 3.6% |
| Neophyl chloride: | 1.9% |
| Unidentified compounds: | 0.7% |
| | 100.0% |

(1) (Methallylbenzene)
(2) (Isobutenylbenzene)

From these numbers, a conversion of chlorine compounds to olefins is calculated of 95.6%. Based on conversion, the yield in olefins is 98.2%.

The olefins are purified by distillation in the following ways:

| Fr. No. | Boiling Range (°C.) | Pressure (mbar) | Wt. (g) | Wt. (%) | Ratio Reflux:Dischg. |
|---|---|---|---|---|---|
| Feed: 217 g | | | | | |
| 1 | 60–71 | 13 | 193 | 90.6 | 5:1 |
| Residue | | | 7 | 3.3 | |
| Column Content | | | 11 | 5.2 | |
| Cooling Trap | | | 2 | 0.9 | |
| | | | 213 | 100.0 | |

The distillate has a chlorine content of 800 ppm and the following composition, according to GC:

| | |
|---|---|
| 1-Phenyl-2-methyl-2-propene (1): | 35.3% |
| 1-Phenyl-2-methyl-1-propene (2): | 63.7% |
| 1-Phenyl-2-methyl-2-chloropropane: | 0.1% |
| Unidentified compounds: | 0.9% |
| | 100.0% |

(1) (Methallylbenzene)
(2) (Isobutenylbenzene)

EXAMPLE 1b—ISOMERIZATION

A glass apparatus is employed consisting of a three-necked flask with stirrer, thermometer, and a glass column, filled with multifil packing elements and having a length of 0.5 m, with a distillation head.

Starting materials:
200 g of distilled olefin mixture containing 94.2% isobutenylbenzene and 5.6% methallylbenzene
10 g of isobutanol
4 g of potassium hydroxide (about 90% strength)
0.2 g of tert-butylpyrocatechol The mixture is agitated under a nitrogen blanket, heated to 185° C.; after 4 hours of agitation at this temperature, distillate is removed and distilled under normal pressure in the following way:

| Fr. No. | Time (h) | Temperatures (°C.) Head | Temperatures (°C.) Sump | Weight (g) | Weight (%) | Ratio Reflux:Dischg. |
|---|---|---|---|---|---|---|
| 1 | 2 | 92–175 | 185–186 | 10 | 4.8 | 10:1 |
| 2 | 6 | 176 | 186 | | | 20:1 |
| | | 178 | 186 | 178 | 84.8 | 10:1 |
| | | 178 | 224 | | | 20:1 |
| 3 | 1 | 182 | 292 | 14 | 6.7 | 5:1 |
| Residue | | | | 7 | 3.3 | |
| Cooling Trap | | | | 1 | 0.4 | |

The chlorine contents of fractions 2 and 3, respectively, are 7 and 10 ppm, respectively.

The table set forth below shows the isobutanol and olefin contents in the three fractions:

| | GC Analysis Data (in %): | | |
|---|---|---|---|
| | Fraction No. | | |
| Compound | 1 | 2 | 3 |
| Isobutanol | 89.0 | 0.1 | 0.1 |
| 1-Phenyl-2-methyl-2-propene (1) | 9.5 | 75.4 | 19.7 |
| 1-Phenyl-2-methyl-1-propene (2) | 0.5 | 24.0 | 80.0 |

(1) (Methallylbenzene)
(2) (Isobutenylbenzene)

The following yield can be calculated, based on these data: The starting compounds are 188.4 g of β-olefin and 11.2 g of α-olefin, yielding 137.3 g of α-olefin and 54.0 g of β-olefin, i.e. 126.1 g of α-olefin is newly formed, or 100 g of β-olefin (100% strength) yields 66.9 g of α-olefin.

By redistillation, the isomers are obtained in a purity of above 99%.

EXAMPLES 2 and 3—ISOMERIZATION

The same apparatus is utilized as described in Example 1b, and the same starting materials are employed, but, in place of 10 g of isobutanol, the same amount of tert-butanol and, respectively, in a further experiment, 10 g of diglycol n-butyl-tert-butyl ether are utilized. For obtaining equally good results as in Example 1b, the isomerization period must be increased from 9 hours to 20 and 46 hours, respectively.

EXAMPLE 4a—THERMAL CRACKING

A glass apparatus is used consisting of a three-necked flask (without a stirrer) including a thermometer, gas sparging tube and reflux condenser.

Starting compounds:
259 g of p-tert-butylneophyl chloride (98.8% strength, mp 50°–52° C.)
0.5 g of tert-butylpyrocatechol The product mixture is heated, and a gentle nitrogen stream is conducted through the melt. Cracking commences at 218° C. After one-half hour, the temperature is 238° C. and, after one hour, 248° C. This temperature is maintained for another 6 hours, i.e. the entire reaction period is 7 hours.

The reaction product has a chlorine content of 240 ppm. Accordingly the conversion is 99.9%. The yield of olefins is 87% of theory, based on the feed.

Analysis by gas chromatography indicates that the cracked product contains p-tert-butylmethallylbenzene in an amount of 13.2% and p-tert-butylisobutenylbenzene in an amount of 78.7%.

EXAMPLE 4b—ISOMERIZATION

The apparatus described in Example 1b is used, with the following compounds:
250 g of olefin mixture containing 78.8% of p-tert-butylisobutenylbenzene 19.5% of p-tert-butylmethallylbenzene
13 g of isobutanol
6.4 g of potassium hydroxide (about 90% strength)
0.5 g of tert-butylpyrocatechol Isomerization takes place under normal pressure as described in Example 1b, obtaining sump temperatures of 232°–300° C. and head temperatures of 88°–240° C. The desired product (218 g) boils at 238°–240° C., has a chlorine content of merely 7 ppm, and contains the following, according to analysis by gas chromatography:

| | |
|---|---|
| p-tert-butylmethallylbenzene | 83.8% |
| p-tert-butylisobutenylbenzene | 14.9% |

The following yield is calculated from these numerical data:
Starting compounds: 197 g of β-olefin and 48.8 g of α-olefin
Product compounds: 182.7 g of α-olefin and 32.5 g of β-olefin
i.e.,
133.9 g of α-olefin is newly formed, or
100.0 g of β-olefin (100% strength) yields
68.0 g of α-olefin.

EXAMPLE 5a—THERMAL CRACKING

The apparatus described in Example 4a is employed, and the following compounds are used for the cracking step:
630 g of p-isopropylneophyl chloride (99.0% strength)
0.5 g of tert-butylpyrocatechol The process is performed as disclosed in Example 4a. Hydrogen chloride evolution starts from 264° C., and the temperature in the flask drops to 236° C. during the course of the thermal cracking reaction on account of the formation of cracked products. The reaction product, 490 g, has a chlorine content of 330 ppm; this content corresponds to a conversion of 99.8%. By redistillation of the crude cracked product, 35 g of high-boiling compounds is separated. The yield of olefin mixture is 88.2% of theory, based on the feed.

According to gas chromatographical analysis, the mixture contains the isomers in the following concentrations:

| | |
|---|---|
| p-isopropylmethallylbenzene | 24.6% |
| p-isopropylisobutenylbenzene | 72.1% |

EXAMPLE 5b—ISOMERIZATION

The apparatus described in Example 1b is employed, and the following compounds are used:

| | |
|---|---|
| 383 g of distilled olefin mixture, containing | |
| p-isopropylmethallylbenzene | 24.6% and |
| p-isopropylisobutenylbenzene | 72.1% |
| 20 g of isobutanol | |
| 9.8 g of potassium hydroxide (about 90% strength) | |
| 0.5 g of tert-butylpyrocatechol | |

The process is performed as described in Example 1b. Within a boiling range of 227°–230° C. under normal pressure, 345 g of a fraction 2, and at 234°–236° C. 23 g of a fraction 3 are obtained, with the following contents of α- and β-olefins, respectively:

| Compound | Fraction No. 2 | Fraction No. 3 |
|---|---|---|
| p-Isopropylmethallylbenzene | 77.1 | 38.3 |
| p-Isopropylisobutenylbenzene | 18.0 | 61.1 |

The chlorine content of fraction 2 is 5 ppm, and the chlorine content of fraction 3 is 8 ppm.

The following yield is calculated from the above numbers:

The starting materials are 276.1 g of β-olefin and 94.2 g of α-olefin, yielding 274.8 g of α-olefin and 76.2 g of β-olefin, i.e. 180.6 g of α-olefin is newly formed, or 100 g of β-olefin yields 65.4 g of α-olefin.

The isomers are obtained in above 99% purity by redistillation.

EXAMPLE 6—THERMAL CRACKING

The apparatus is utilized which is disclosed in Example 1a, and the following products are used as feed:
150 g of p-methylneophyl chloride (98.5% strength)
0.5 g of hydroquinone The thermal cracking step is conducted under normal pressure as described in Example 1a.

The conversion, calculated from the chlorine content of the cracked product, is 96.0%. Based on conversion, the yield of olefins is 97.0%.

After purification by distillation, the chlorine content is 530 ppm. According to GC analysis, the distillate contains the isomers in the following concentrations:

| | |
|---|---|
| p-methylmethallylbenzene | 31.2% |
| p-methylisobutenylbenzene | 65.8% |

EXAMPLE 7—THERMAL CRACKING

With the apparatus described in Example 1a, the following compounds are utilized:
200 g of p-ethylneophyl chloride (98.7% strength)
2 g of 2,6-di-tert-butylphenol Thermal cracking is conducted under normal pressure as described in Example 1a.

Conversion, calculated from the chlorine content of the cracked product, is 97.1%. Based on conversion, the yield of olefins is 98.5%.

After purification by distillation, the chlorine content is 310 ppm.

The isomers are present in the distillate in the following concentrations:

| | |
|---|---|
| p-ethylmethallylbenzene | 30.7% |
| p-ethylisobutenylbenzene | 66.4% |

EXAMPLE 8—ISOMERIZATION

The apparatus is used as described in Example 1b, and the olefin mixture mentioned therein is employed, together with the following compounds:

| | |
|---|---|
| 250 g of olefin mixture | |
| 6 g of sodium hydroxide | |
| 30 g of n-butyl diglycol | |
| 30 g of isobutanol | |
| 0.5 g of tert-butylpyrocatechol | |

The process is conducted as described in Example 1b. The result is very similar: The isomerization period is about 10 hours. The distillate has a chlorine content of 6 ppm. The yield from 100 g of β-olefin is 66.1 g of α-olefin.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a substantially pure mixture of methallyl-p-R-benzene (α-isomer), and the corresponding isobutenyl-p-R-benzene (β-isomer) by thermally cracking the corresponding p-R-neophyl chloride, wherein R is H or $C_1$–$C_4$-alkyl, the improvement comprising
   thermally cracking the neophyl chloride compound in the presence of an effective amount of an inhibitor of free radical polymerization of olefins and isomerizing the formed β-olefin by heating it thereby forming the corresponding α-olefin.

2. A process of claim 1, wherein the inhibitor is tert-butylpyrocatechol, hydroquinone, or 2,6-di-tert-butylphenol.

3. A process of claim 1, wherein R is H, $CH_3$, $CH_3CH_2—$, $—CH(CH_3)_2$ or $—C(CH_3)_3$.

4. A process of claim 1 for increasing the yield of the α-olefin comprising isomerizing the formed β-olefin by heating it at about 80°–300° C. thereby forming the corresponding α-olefin.

5. A process as claimed in claim 4, wherein the isomerization is conducted in the presence of an amount of a strong base effective to increase the amount of α-olefin obtained.

6. A process of claim 5, wherein the isomerization is further conducted in the presence of a polar solvent.

7. A process of claim 5, wherein the isomerization is conducted under conditions of fractional distillation.

8. A process of claim 6, wherein the isomerization is conducted under conditions of fractional distillation.

9. A process as claimed in claim 6, wherein the isomerization is conducted in the further presence of an inhibitor of free radical polymerization of olefins.

10. A process as claimed in claim 8, wherein the isomerization is conducted in the further presence of an inhibitor of free radical polymerization of olefins.

11. A process of claim 6, wherein R is H, $CH_3$, $CH_3CH_2—$, $—CH(CH_3)_2$ or $—C(CH_3)_3$.

12. A process as claimed in claim 6, wherein the inhibitor is tert-butylpyrocatechol, hydroquinone, or 2,6-di-tert-butylphenol.

13. A process as claimed in claim 6, wherein the inhibitor concentration ranges from about 0.01 to 5%.

14. A process according to claim 6, wherein the basic compound is selected from class of alkali metal hydroxides.

15. A process according to claim 6, wherein the basic compound is sodium hydroxide or potassium hydroxide.

16. A process according to claim 6, wherein the polar solvent is a high boiling alcohol or a polar aprotic compound.

17. A process according to claim 6, wherein the polar aprotic compound is dimethyl sulfoxide, dimethylformamide, N-methylpyrrolidone, an alkyl glycol ether with a $C_1$- to $C_4$-alkyl group, a polyglycol or a polyethylene glycol diether of the formula $R—O(—CH_2—CH_2O)_n-R$ wherein n=1 to 20 and $R=C_{1-4}$-alkyl.

18. A process as claimed in claim 6, wherein the basic compound is present in amounts from 0.1 to 50%.

19. A process as claimed in claim 2, wherein the polar solvent is present in about 1 to 50%.

20. A process as claimed in claim 6, wherein the isomerization is conducted at temperatures ranging from about 180°–300° C.

21. A process according to claim 1, wherein the temperature of the cracking step is 150°–350° C.

22. A process as claimed in claim 6, wherein the process is a batch process.

23. A process as claimed in claim 1, wherein the thermal cracking is performed at pressures ranging from 1–20 bar.

24. A process for isomerizing isobutenyl-p-R-benzene to methallyl-p-R-benzene comprising heating the former in the presence of a strong base, the temperature and base strength and amount being effective for said isomerization.

25. A process according to claim 24, wherein the isomerization is conducted in the presence of a polar solvent.

* * * * *